US010939093B2

(12) United States Patent
Kujuuro et al.

(10) Patent No.: US 10,939,093 B2
(45) Date of Patent: Mar. 2, 2021

(54) IMAGE PROCESSING DEVICE FOR ENDOSCOPE THAT RECONFIGURES IMAGE PROCESSING CIRCUIT BASED ON DISCONNECTION TIME

(71) Applicant: OLYMPUS CORPORATION, Tokyo (JP)

(72) Inventors: Yosuke Kujuuro, Yokohama (JP); Tomoki Iwasaki, Fuchu (JP); Kenji Yamazaki, Hino (JP); Susumu Hashimoto, Hachioji (JP); Kyosuke Mizuno, Hino (JP); Hiroshi Shiraishi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 3 days.

(21) Appl. No.: 16/382,277

(22) Filed: Apr. 12, 2019

(65) Prior Publication Data
US 2019/0238831 A1   Aug. 1, 2019

Related U.S. Application Data

(63) Continuation of application No. PCT/JP2017/034920, filed on Sep. 27, 2017.

(30) Foreign Application Priority Data

Oct. 14, 2016   (JP) .............................. JP2016-202983

(51) Int. Cl.
*H04N 17/00* (2006.01)
*G02B 23/24* (2006.01)
(Continued)

(52) U.S. Cl.
CPC ............. *H04N 17/002* (2013.01); *A61B 1/04* (2013.01); *G02B 23/24* (2013.01); *H04N 7/18* (2013.01); *H04N 2005/2255* (2013.01)

(58) Field of Classification Search
CPC ........ A61B 1/04; G02B 23/24; H04N 17/002; H04N 2005/2255; H04N 7/18
See application file for complete search history.

(56) References Cited

U.S. PATENT DOCUMENTS

2003/0160865 A1\* 8/2003 Takahashi .............. H04N 7/183
348/65
2008/0143827 A1   6/2008 Yoshizumi et al.
(Continued)

FOREIGN PATENT DOCUMENTS

JP    H11-298907 A    10/1999
JP    2003-319905 A   11/2003
(Continued)

OTHER PUBLICATIONS

International Search Report dated Nov. 14, 2017 issued in PCT/JP2017/034920.
(Continued)

*Primary Examiner* — Francis Geroleo
(74) *Attorney, Agent, or Firm* — Scully, Scott, Murphy & Presser, P.C.

(57) ABSTRACT

A processing device includes a processing circuit configurable according to a type of an endoscope, and a control circuit configured to detect a connection state of the endoscope, and measure a disconnection time from disconnection to reconnection. The control circuit is also configured to determine that currently and previously connected endoscopes are of the same type when the disconnection time is shorter than a predetermined time, reconfigure the processing circuit according to the type of the endoscope when it is determined that the currently and previously connected endoscopes are not of the same type, and not reconfigure the processing circuit when it is determined that the currently and previously connected endoscopes are of the same type.

7 Claims, 4 Drawing Sheets

(51) Int. Cl.
    *A61B 1/04*     (2006.01)
    *H04N 7/18*     (2006.01)
    *H04N 5/225*     (2006.01)

(56) References Cited

U.S. PATENT DOCUMENTS

| 2011/0175990 | A1* | 7/2011 | Sato | H04N 7/183 |
| | | | | 348/65 |
| 2013/0141557 | A1* | 6/2013 | Kawata | A61B 1/00059 |
| | | | | 348/65 |

FOREIGN PATENT DOCUMENTS

| JP | 2007-229305 A | 9/2007 |
| JP | 2008-149027 A | 7/2008 |
| JP | 2011-147548 A | 8/2011 |
| JP | 2013-009908 A | 1/2013 |
| WO | WO 2016/076314 A1 | 5/2016 |

OTHER PUBLICATIONS

English translation of International Preliminary Report on Patentability dated Apr. 25, 2019, together with the Written Opinion received in related International Application No. PCT/JP2017/034920.

* cited by examiner

IMAGE PROCESSING DEVICE FOR ENDOSCOPE THAT RECONFIGURES IMAGE PROCESSING CIRCUIT BASED ON DISCONNECTION TIME

CROSS-REFERENCE TO RELATED APPLICATIONS

This application is a Continuation Application of PCT Application No. PCT/JP2017/034920, filed Sep. 27, 2017 and based upon and claiming the benefit of priority from prior Japanese Patent Application No. 2016-202983, filed Oct. 14, 2016, the entire contents of all are here now reference.

BACKGROUND OF THE INVENTION

1. Field of the Invention

The present invention relates to an image processing device for an endoscope.

2. Description of the Related Art

Known have been electronic endoscopes comprising imaging elements such as CCD image sensors at the distal ends. Image processing devices that process image data obtained by such endoscopes and create a display image are configured so that different types of endoscopes can be connected. In an image processing device to which different types of endoscopes can be connected, settings are made according to the endoscope that is connected.

For example, Jpn. Pat. Appln. KOKAI Publication No. 2008-149027 discloses a technique relating to an image processing device having the following functions. That is, the image processing device obtains a scope ID from the endoscope that is equipped with a CCD image sensor. The image processing device reads corresponding parameters from a table which is storing image processing parameters according to the type of the endoscope. The image processing device writes data into registers for various functional modules in the image processor based on the read parameters. The various functional modules perform image processing corresponding to the connected scope according to the written parameters.

In recent years, the image processing function of endoscopic systems has been improved, and the scale of the circuit used for the processing has increased. Consequently, the time required for reconfiguring the circuit during the initial setting tends to increase.

BRIEF SUMMARY OF THE INVENTION

An image processing device includes an image processing circuit configured to process image data obtained from an endoscope. The image processing circuit is configurable according to a type of the endoscope. The image processing device further includes at least one control circuit configured to detect a connection state of the endoscope, and measure, based on a detection result of the connection state, a disconnection time from when the endoscope is disconnected until the endoscope is reconnected. The control circuit is also configured to determine, when the disconnection time is shorter than a predetermined time, that a currently connected endoscope and a previously connected endoscope are of a same type, reconfigure the image processing circuit according to the type of the endoscope when it is determined that the currently connected endoscope and the previously connected endoscope are not of the same type, and not reconfigure the image processing circuit when it is determined that the currently connected endoscope and the previously connected endoscope are of the same type.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

A first embodiment of the present invention will be described with reference to the drawings. The endoscopic system according to the first embodiment is a system capable of connecting different types of endoscopes to the image processing device. The user connects the endoscope that is selected according to the application to the image processing device and then uses the endoscope. The image processing device performs different image processes depending on the connected endoscope and then displays an endoscopic image.

Configuration of the Endoscopic System

Figure 1:
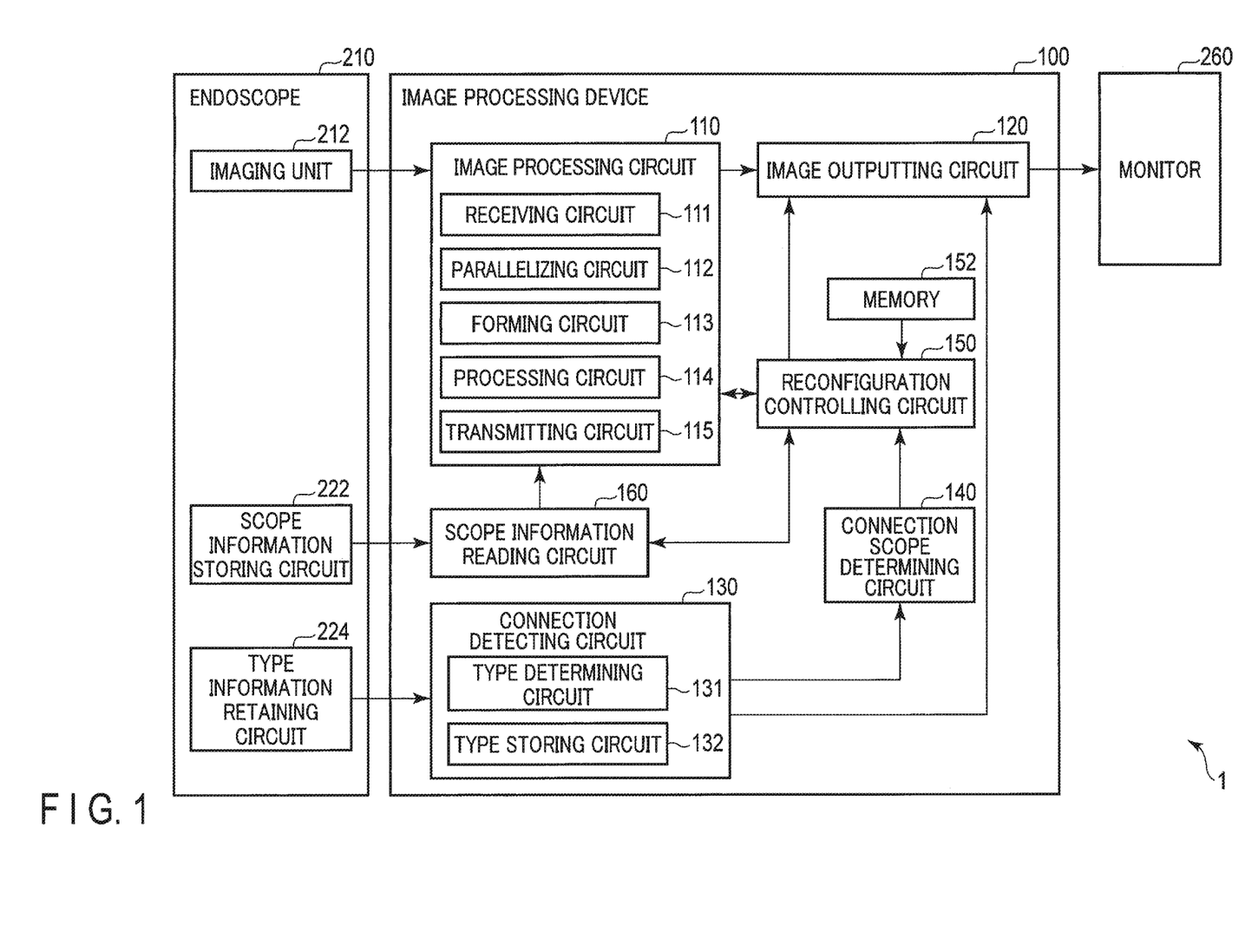
FIG. 1 is a block diagram schematically showing a configuration example of the endoscopic system according to a first embodiment.

FIG. 1 schematically shows a configuration example of an endoscopic system 1 according to the first embodiment. As shown in FIG. 1, the endoscopic system 1 comprises an endoscope 210, an image processing device 100, and a monitor 260. The endoscope 210 is, for example, a flexible endoscope for medical treatment, although it is not limited thereto. The image processing device 100 performs various image processes to the image data that is obtained by the imaging by the endoscope 210. The monitor 260 includes, for example, a liquid crystal display or the like. The monitor 260 displays an image based on image data to which the image processing has been performed by the image processing device 100.

In the endoscopic system 1, different types of endoscopes may be connected to the image processing device 100. The user uses the endoscopic system 1 by connecting the endoscope of a type corresponding to the application to the image processing device 100. Therefore, the endoscope 210 and the image processing device 100 can be disconnected. The configuration shown in FIG. 1 is not limited to the type of the endoscope. It is rather common to all types of endoscopes.

Neither the connection nor the disconnection of the endoscope 210 to the image processing device 100 is limited to being performed during the time of exchanging the endoscope 210. If the cable connecting the endoscope 210 to the image processing device 100 becomes twisted during the usage of the endoscope 210, the user may perform, for example, the following operations to untwist the cable. That is, the user may disconnect the cable from the image processing device 100, then untwist the cable, and then reconnect the cable to the image processing device 100.

The endoscope 210 comprises an elongated insertion section configured to be inserted, for example, into the body. At the distal end of the insertion section, an imaging unit 212 is provided that includes, for example, a CCD image sensor. The imaging unit 212 generates image data. This image data is transmitted to the image processing device 100 to undergo various processes by the image processing device 100.

The endoscope 210 includes a scope information storing circuit 222 and a type information retaining circuit 224. The scope information storing circuit 222 includes, for example, a memory. The scope information storing circuit 222 stores scope information necessary for setting the endoscope 210. The type information retaining circuit 224 retains information regarding the type of the endoscope 210. The type information retaining circuit 224 may include, for example, a memory or the like in which type information is recorded. In addition, the type information retaining circuit 224 includes, for example, a resistance element having a predetermined resistance value predetermined for each type, and the type may be discriminated by reading this resistance value.

The image processing device 100 includes an image processing circuit 110, an image outputting circuit 120, a connection detecting circuit 130, a connection scope determining circuit 140, a reconfiguration controlling circuit 150, a nonvolatile memory 152, and a scope information reading circuit 160. The functions of the image processing circuit 110, the image outputting circuit 120, the connection detecting circuit 130, the connection scope determining circuit 140, the reconfiguration controlling circuit 150, the scope information reading circuit 160, and the like are implemented by using an integrated circuit or the like. The image processing circuit 110, the image outputting circuit 120, the connection detecting circuit 130, the connection scope determining circuit 140, the reconfiguration controlling circuit 150, the scope information reading circuit 160, and the like may be fabricated by using a single integrated circuit as well as by using a plurality of integrated circuits. In the first embodiment, at least the image processing circuit 110 is fabricated by a configurable circuit such as, for example, a field-programmable gate array (FPGA).

The image processing circuit 110 obtains image data from the imaging unit 212 of the endoscope 210. The image processing circuit 110 performs various processes to the obtained image data, and transmits the processed image data to the image outputting circuit 120. Note that the image processing circuit 110 includes a receiving circuit 111, a parallelizing circuit 112, a forming circuit 113, a processing circuit 114, and a transmitting circuit 115. The receiving circuit 111 obtains image data from the imaging unit 212. The parallelizing circuit 112 parallelizes image data received as serial data, for example, in parallel for each color. The forming circuit 113 performs, for example, image forming or the like. The processing circuit 114 performs data processing relating to the image such as noise removal, amplification, and the like. The transmitting circuit 115 converts the processed data into an appropriate data format and outputs it to the image outputting circuit 120. The processing performed in the image processing circuit 110 varies depending on the type of the endoscope 210 connected to the image processing device 100. Therefore, the configuration of the image processing circuit 110 in the first embodiment is reconfigured according to the type of the endoscope 210.

The image outputting circuit 120 transmits the image data obtained from the image processing circuit 110 after the image processing to the monitor 260 outside the image processing device 100 and causes the monitor 260 to display an image based on the image data.

The connection detecting circuit 130 determines whether or not the endoscope 210 is connected to the image processing device 100. The connection detecting circuit 130 includes a type determining circuit 131 and a type storing circuit 132. The connection detecting circuit 130 obtains, from the type information retaining circuit 224 of the endoscope 210, information regarding the type of the endoscope 210 connected to the image processing device 100. Based on this information, the type determining circuit 131 determines the type of the connected endoscope 210 when the endoscope 210 is connected to the image processing device 100. The type storing circuit 132 stores information on the determined type of the endoscope 210. That is, the type storing circuit 132 stores the type of the endoscope 210 previously connected to the image processing device 100. Further, the connection detecting circuit 130 transmits, to the image outputting circuit 120, information regarding the circumstance that the endoscope 210 is not connected to the image processing device 100, such information being, for example, that the endoscope 210 has been removed from the image processing device 100. Based on this information, the image outputting circuit 120 stops outputting data to the monitor 260 when the endoscope 210 is not connected to the image processing device 100.

The connection scope determining circuit 140 compares the type of the currently connected endoscope 210 determined by the type determining circuit 131 to the type of the previously connected endoscope 210 stored in the type storing circuit 132 to determine whether the currently connected endoscope 210 and the previously connected endoscope 210 are of the same type. When it is determined that the currently connected endoscope 210 and the previously connected endoscope 210 are not of the same type, i.e., are of different types, the connection scope determining circuit 140 transmits information relating to the type of the currently connected endoscope 210 to the reconfiguration controlling circuit 150 so that the image processing circuit 110 is reconfigured according to the currently connected endoscope 210. Vice versa, when it is determined that the currently connected endoscope 210 and the previously connected endoscope 210 are of the same type, the connection scope determining circuit 140 transmit a message to the reconfiguration controlling circuit 150 to the effect that reconfiguration of the image processing circuit 110 is unnecessary.

When information indicating that reconfiguration of the image processing circuit 110 is necessary is obtained from the connection scope determining circuit 140, the reconfiguration controlling circuit 150 reconfigures the image processing circuit 110. At this point, the reconfiguration controlling circuit 150 obtains information on the type of the endoscope 210 connected to the image processing device 100 from the connection scope determining circuit 140, and obtains setting information corresponding to the type from the memory 152. The reconfiguration controlling circuit 150 reconfigures the image processing circuit 110 based on the obtained setting information. Vice versa, when information is obtained from the connection scope determining circuit 140 indicating that reconfiguration of the image processing circuit 110 is unnecessary, the reconfiguration controlling circuit 150 does not reconfigure the image processing circuit 110.

The memory 152 stores various types of information necessary for processing the image processing device 100. The information stored in the memory 152 includes information on the reconfiguration of the image processing circuit 110. In addition, the information stored in the memory 152 may include information other than information related to circuit reconfiguration, namely information related to setting the image processing circuit 110. Information on reconfiguration and setting of the image processing circuit 110 can be read by the reconfiguration controlling circuit 150.

The reconfiguration controlling circuit 150 causes the image processing circuit 110 to configure a circuit in accordance with the special function of the endoscope 210, for example, the type of imaging element used for the imaging unit 212 of the endoscope 210 or the endoscope 210 being a three-dimensional endoscope.

When the endoscope 210 is connected to the image processing device 100, the scope information reading circuit 160 obtains the scope information related to the setting of the endoscope 210 from the scope information storing circuit 222 of the endoscope 210. The scope information reading circuit 160 further performs various settings of the image processing circuit 110 based on the obtained scope information. The setting performed here may also include settings related to adjustment of the individual differences of the endoscope 210. This setting may include, for example, correction related to the individual dispersion, correction of imaging element defects, shading correction, and the like. The scope information reading circuit 160 may use the information stored in the memory 152 for setting the image processing circuit 110.

Note that while the reconfiguration controlling circuit 150 reconfigures the image processing circuit 110 and performs various settings, the reconfiguration controlling circuit 150 informs the image outputting circuit 120 of these circumstances, and causes the image outputting circuit 120 to stop outputting data to the monitor 260.

Image Processing Device Operations

Figure 2:
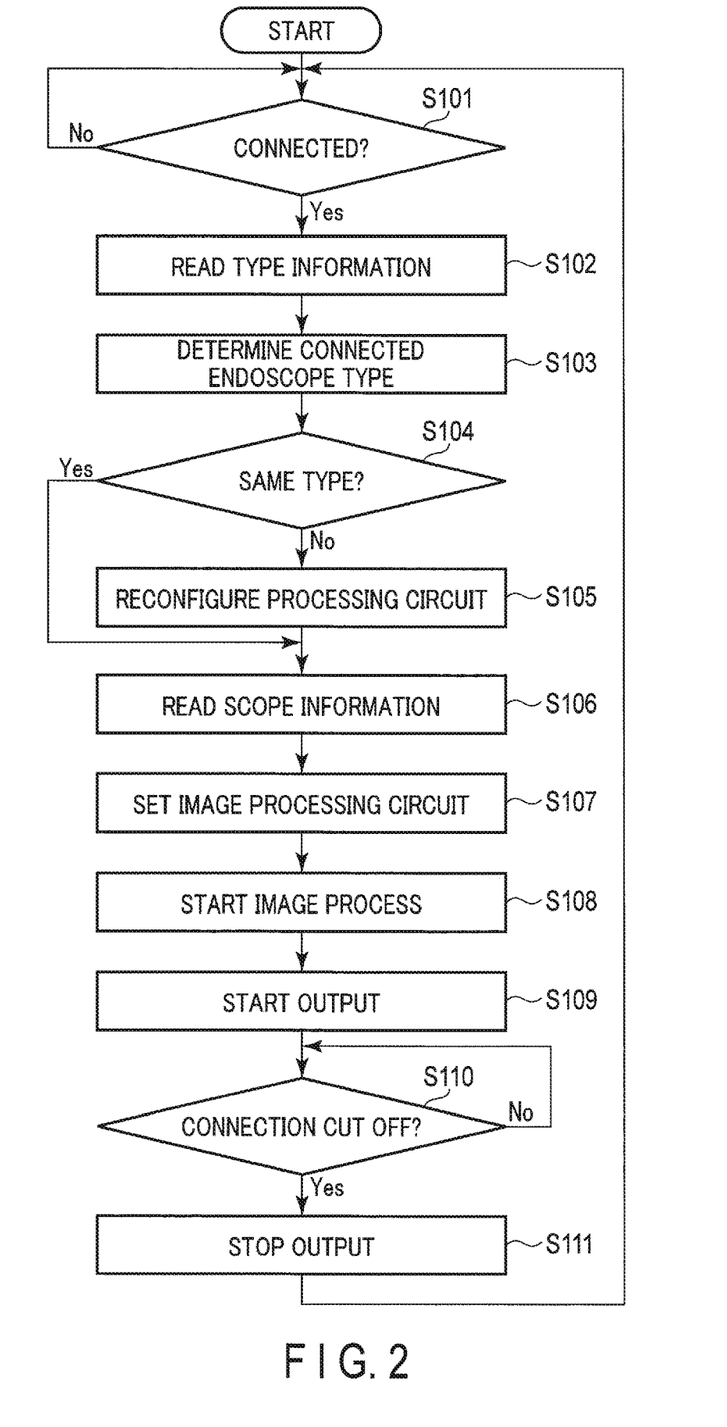
FIG. 2 is a flowchart showing an example of processing in the image processing device according to the first embodiment.

FIG. 2 is a flowchart showing an example of an initial setting process performed when the endoscope 210 is connected to the image processing device 100, and operations related to the subsequent image output. The process starts when, for example, the image processing device 100 is powered on, and terminates when it is powered off.

In step S101, the connection detecting circuit 130 of the image processing device 100 determines whether or not the endoscope 210 is connected to the image processing device 100. If the endoscope 210 is not connected to the image processing device 100, step S101 is repeated in stand-by. If the endoscope 210 is connected to the image processing device 100, the process continues to step S102.

In step S102, the connection detecting circuit 130 of the image processing device 100 reads the type information from the type information retaining circuit 224 of the endoscope 210. At this point, if the operation is performed for the second or subsequent time and the image processing circuit 110 processes the image, the image processing circuit 110 stops the image processing operation due to the setting of the image processing circuit 110 to be performed afterward.

In step S103, the type determining circuit 131 of the connection detecting circuit 130 of the image processing device 100 determines the type of the endoscope 210 connected to the image processing device 100 based on the read type information. The type of the endoscope 210 determined here is appropriately stored in the type storing circuit 132.

In step S104, the connection scope determining circuit 140 of the image processing device 100 determines whether or not the endoscope 210 connected to the image processing device 100 is the same type as the previously connected endoscope 210. In this case, the connection scope determining circuit 140 performs the determination by comparing the type of the currently connected endoscope 210 determined by the type determining circuit 131 of the connection detecting circuit 130 with the type of the previously connected endoscope 210 stored in the type storing circuit 132. When the type of the currently connected endoscope 210 is the same as the type of the previously connected endoscope 210, the process continues to step S106. Vice versa, when the type of the currently connected endoscope 210 is not the same as the type of the previously connected endoscope 210, the process continues to step S105.

In step S105, the reconfiguration controlling circuit 150 of the image processing device 100 reconfigures the image processing circuit 110. Here, the reconfiguration controlling circuit 150 obtains information related to the type of the connected endoscope 210 from the connection scope determining circuit 140. The reconfiguration controlling circuit 150 obtains, from the memory 152, information relating to the circuit of the image processing circuit 110 corresponding to the obtained type of the endoscope 210. The reconfiguration controlling circuit 150 reconfigures the circuit configuration of the image processing circuit 110 by changing the same based on the information on this circuit. Upon completion of the reconfiguration of the circuit of the image processing circuit 110, the process continues to step S106.

In step S106, the scope information reading circuit 160 of the image processing device 100 reads the scope information on the endoscope 210 from the scope information storing circuit 222 of the endoscope 210.

In step S107, the scope information reading circuit 160 of the image processing device 100 sets the image processing circuit 110. In this case, the scope information reading circuit 160 uses the scope information obtained from the scope information storing circuit 222, or it uses the information read from the memory 152 based on the scope information. Upon completion of the setting of the image processing circuit 110, the process continues to step S108.

In step S108, the image processing circuit 110 of the image processing device 100 starts image processing of the set contents for the image data input from the endoscope 210. That is, the image processing circuit 110 sequentially obtains the image data obtained by the imaging of the imaging unit 212, then sequentially performs set image processing for the obtained image data, and then sequentially transmits the processed image data to the image outputting circuit 120. The image processing circuit 110 continues such image processing afterwards.

In step S109, the reconfiguration controlling circuit 150 of the image processing device 100 causes the image outputting circuit 120 to start outputting, to the monitor 260, image data that is based on the data input from the image processing circuit 110. As a result, the image processed by the image processing circuit 110 is continuously displayed on the monitor 260 afterwards.

In step S110, the connection detecting circuit 130 of the image processing device 100 determines whether or not the connection of the endoscope 210 to the image processing device 100 has been cut off. Until the connection is cut off, the image obtained by the imaging unit 212 of the endoscope 210 and processed by the image processing circuit 110 is displayed on the monitor 260. If the endoscope 210 is disconnected from the image processing device 100 and the connection is cut off, the process continues to step S111.

In step S111, the connection detecting circuit 130 of the image processing device 100 causes the image outputting circuit 120 to stop outputting images to the monitor 260. Subsequently, the process returns to step S101. That is, the above process is repeated. This process is repeated until the power of the image processing device 100 is turned off. As described above, the type of the currently connected endoscope 210 is compared with the type of the previously connected endoscope 210, and if the types are different, the reconfiguration controlling circuit 150 performs the reconfiguration process. If the types are the same, the reconfiguration controlling circuit 150 does not perform the reconfiguration process.

Figure 3:
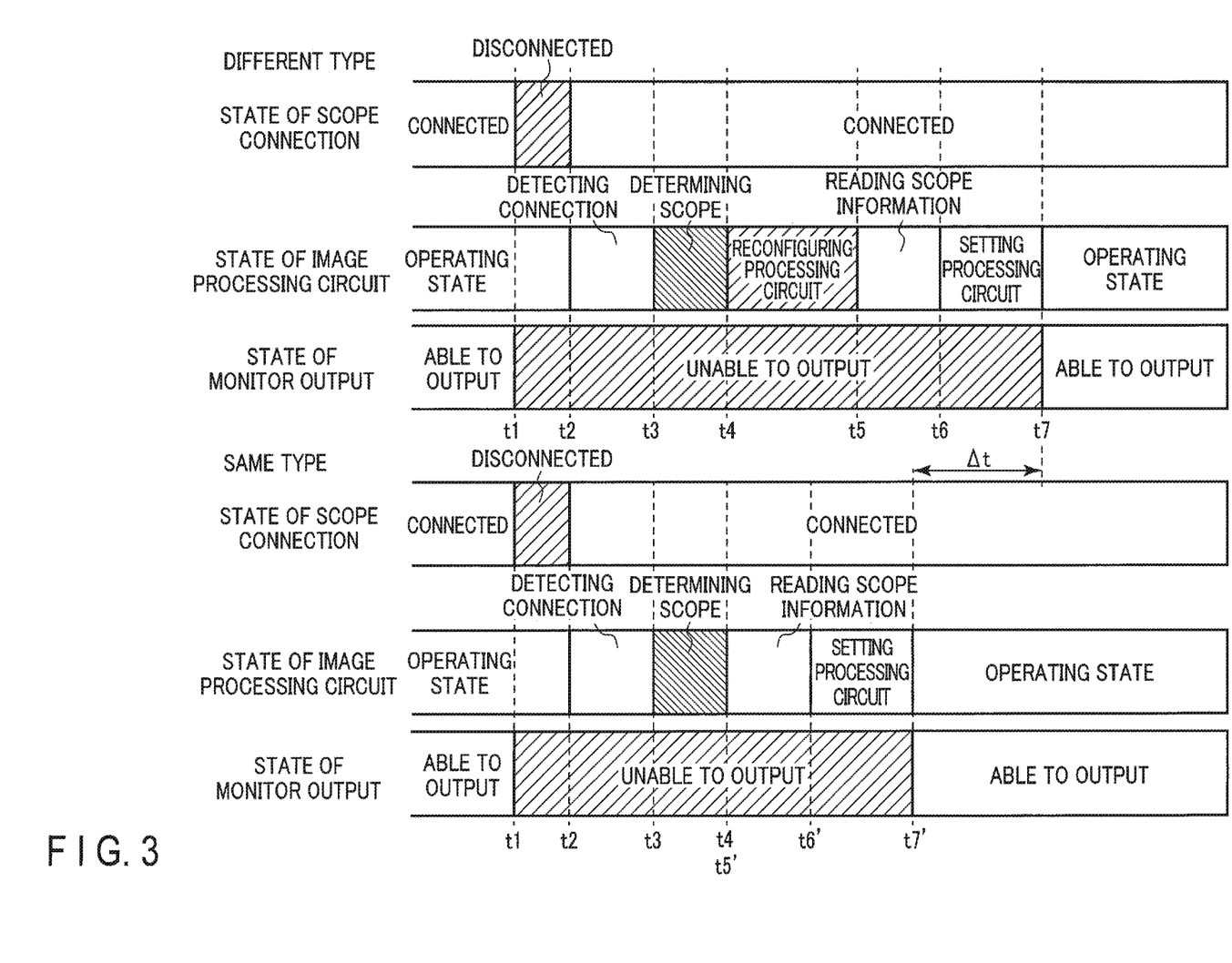
FIG. 3 is a timing chart showing an example of processing in the endoscopic system according to the first embodiment.

The operation of the endoscopic system 1 according to the first embodiment will be described with reference to a timing chart shown in FIG. 3. The upper section of FIG. 3 shows a timing chart of an example of processing when the type of the currently connected endoscope is different from the type of the endoscope previously connected to the image processing device 100. The lower section of FIG. 3 shows a timing chart of an example of processing when the type of the currently connected endoscope is the same as the type of the endoscope previously connected to the image processing device 100. In each of the upper section and the lower section of FIG. 3, the first row shows the connection state of the endoscope 210 to the image processing device 100, the second row shows the state of the processing relating to the image processing circuit 110, and the third row shows the state of outputting the image to the monitor 260.

First, with reference to the upper section of FIG. 3, the case will be described in which the types of the previously and the currently connected endoscope 210 are different. As shown in the upper section of FIG. 3, it is assumed that the endoscope 210 is initially connected to the image processing device 100, that the image processing circuit 110 of the image processing device 100 performs the image processing operation, and that the processed image is output to the monitor 260.

Here, it is assumed that the endoscope 210 is disconnected from the image processing circuit 110 at time t1, and that the connection between the image processing circuit 110 and the endoscope 210 is cut off. In this case, the connection detecting circuit 130 causes the image outputting circuit 120 to stop outputting images. As a result, no image is displayed on the monitor 260.

After this, it is assumed that the endoscope 210 is connected to the image processing device 100 at time t2. At this time, the connection detecting circuit 130 detects a connection of the endoscope 210 during the period from time t2 to time t3, and obtains the type information of the endoscope 210 from the type information retaining circuit 224 to determine the type of the endoscope 210. In the period from time t3 to time t4, the connection scope determining circuit 140 determines whether or not the type of the connected endoscope 210 is the same as the type of the previously connected endoscope. Since the types of the previously and the currently connected endoscope 210 are different, the reconfiguration controlling circuit 150 reconfigures the circuit of the image processing circuit 110. The period during which this reconfiguration is performed is from time t4 to time t5. At time t5, reconfiguration of the image processing circuit 110 is completed.

Subsequently, in the period from time t5 to time t6, the scope information reading circuit 160 reads the scope information from the scope information storing circuit 222 of the endoscope 210. In the period from time t6 to time t7, the scope information reading circuit 160 sets the image processing circuit 110. At time t7, the setting of the image processing circuit 110 is completed. After time t7, the image processing circuit 110 performs image processing on the image data. After time t7, the reconfiguration controlling circuit 150 causes the image outputting circuit 120 to output the image. As a result, the image processed by the image processing circuit 110 is displayed on the monitor 260.

Next, with reference to the lower section of FIG. 3, the case will be described in which the types of the previously and the currently connected endoscope 210 are the same. As shown in the lower section of FIG. 3, it is assumed that the endoscope 210 is initially connected to the image processing device 100, that the image processing circuit 110 of the image processing device 100 performs the image processing operation, and that the processed image is output to the monitor 260. Here, it is assumed that the connection between the image processing circuit 110 and the endoscope 210 is cut off at time t1. At this time, the connection detecting circuit 130 causes the image outputting circuit 120 to stop outputting images. As a result, no image is displayed on the monitor 260. It is assumed that the endoscope 210 is connected to the image processing device 100 at time t2. At this time, the connection detecting circuit 130 detects a connection of the endoscope 210 during the period from time t2 to time t3, and obtains the type information of the endoscope 210 from the type information retaining circuit 224 to determine the type of the endoscope 210. During the period from time t3 to time t4 (t5'), the connection scope determining circuit 140 determines whether or not the type of the connected endoscope 210 is the same as the type of the previously connected endoscope.

Since the types of the previously and the currently connected endoscope 210 are the same, the reconfiguration controlling circuit 150 does not reconfigure the circuit of the image processing circuit 110. During the period from time t5' to t6', the scope information reading circuit 160 reads the scope information from the scope information storing circuit 222 of the endoscope 210 and sets the image processing circuit 110 during the period from time t6' to t7'. At time t7', the setting of the image processing circuit 110 is completed, and after time t7', the image processing circuit 110 performs image processing on the image data, and the image processed by the image processing circuit 110 is displayed on the monitor 260.

Comparing the upper section with the lower section of FIG. 3, the upper section of FIG. 3 requires time to reconfigure the circuit of the image processing circuit 110 from time t4 to time t5. However, in the lower section of FIG. 3, this process is omitted. As a result, the time at which the image starts to be displayed on the monitor 260 is time t7 in the case of the upper section of FIG. 3, while it is time t7' in the case of the lower section of FIG. 3. That is, as expressed by Δt in FIG. 3, in the case of the lower section of FIG. 3, the image is displayed earlier on the monitor 260 by the time relating to the reconfiguration of the circuit of the image processing circuit 110.

According to the present embodiment, since the image processing device 100 does not need to reconfigure the image processing circuit 110 in the case where the connected endoscope 210 is of the same type as the previously connected endoscope 210, the image processing device 100 does not perform the reconfiguration. As a result, the time from when the endoscope 210 is connected to the image processing device 100 until the image is displayed on the monitor 260 is necessarily shorter than when the image processing circuit 110 is reconfigured.

In the first embodiment, as compared to the case in which reconfiguration of the image processing circuit 110 is always performed, the time from when the endoscope 210 is connected to the image processing device 100 until the image is displayed on the monitor 260 increases by the amount of time from time t3 to time t4 shown in FIG. 3 related to the process of determining the type of connected endoscope 210. However, this time is relatively short. On the other hand, the time needed for reconfiguring the circuit of the image processing circuit 110 from time t4 to time t5 shown in the upper section of FIG. 3 is relatively long, which is why it is effective to omit this reconfiguration when the same type of the endoscope 210 is connected. Particularly, in cases in which the endoscope 210 is temporarily disconnected and then reconnected in order to avoid twisting of the cable connecting the endoscope 210 to the image processing device 100, the user wants to confirm the image on the monitor 260 as quickly as possible because the endoscope 210 is being used. Display on the monitor 260 is started earlier in such a case, which is why the first embodiment is so effective. Here, the time required for reconfiguration and shortening can be on the order of, for example, several hundred milliseconds or more. Note that since the time required for the reconfiguration increases as the circuit scale of the image processing circuit 110 increases, the time needed for reconfiguration and the time that can be shortened increases the more complex the process has to be.

Modification

In the above embodiment, the image processing circuit 110 is configured by an FPGA and the example given is a case in which the configuration of the circuit of the image processing circuit 110 is physically reconfigured. However, the reconfiguration is not limited to such. That is, the above-described technique may be applied not only when hardware is reconfigured, but also when software is reconfigured. For example, the above-described technique can be applied even when the image processing circuit 110 is implemented using a digital signal processor (DSP). That is, the reconfiguration controlling circuit 150 may, as reconfiguration, write a program corresponding to the type of the endoscope 210 in a dedicated area of the DSP during the activation. The image processing device 100 can be configured such that if the types of the previously and the currently connected endoscope 210 are different, the program is rewritten, and such that the program is not rewritten if the types are the same. Even with such a configuration, the same effects as in the above-described embodiment are achievable.

Second Embodiment

A second embodiment and its differences from the first embodiment will be described. Parts that are the same will be denoted by the same reference symbols and description of the same will be omitted. In the first embodiment, the connection scope determining circuit 140 determines whether or not the type of the currently connected endoscope 210 determined by the type determining circuit 131 coincides with the type of the previously connected endoscope 210 stored in the type storing circuit 132 of the connection detecting circuit 130. In contrast to this, the connection scope determining circuit 140 according to the second embodiment determines, based on the time during which the endoscope 210 is not connected to the image processing device 100, whether or not the type of the currently connected endoscope 210 is the same as the type of the previously connected endoscope 210.

Figure 4:
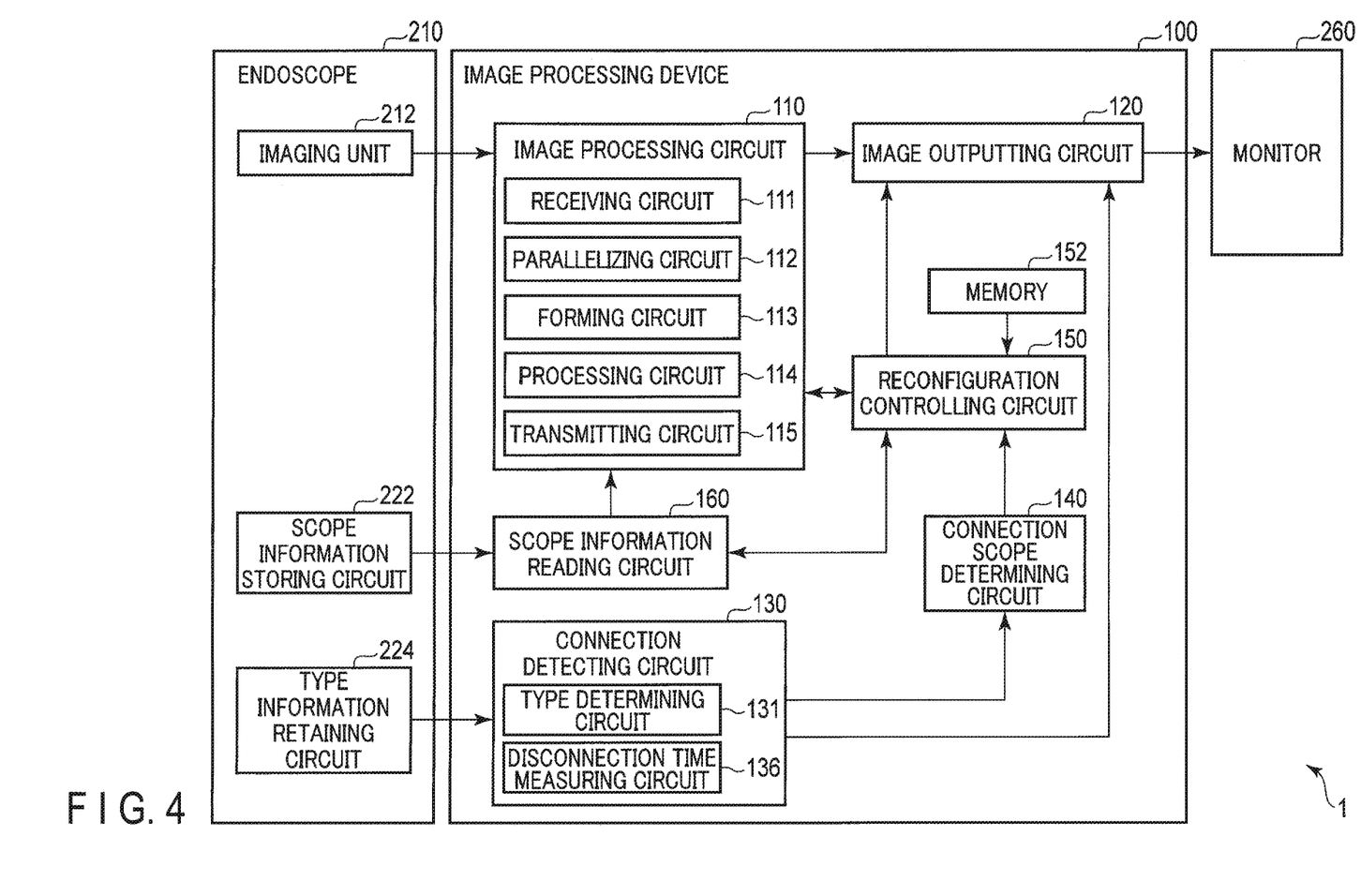
FIG. 4 is a block diagram schematically showing a configuration example of the endoscopic system according to a second embodiment.

FIG. 4 schematically shows a configuration example of the endoscopic system 1 according to the second embodiment. In the endoscopic system 1 according to the second embodiment, the connection detecting circuit 130 of the image processing device 100 is provided with a disconnection time measuring circuit 136 instead of the type storing circuit 132 provided in the first embodiment. The disconnection time measuring circuit 136 measures a disconnection time from when the endoscope 210 is disconnected from the image processing device 100 until the endoscope 210 is reconnected. The disconnection time measuring circuit 136 transmits the information on the obtained disconnection time to the connection scope determining circuit 140.

If the disconnection time is shorter than a predetermined time, the connection scope determining circuit 140 determines that the type of the currently connected endoscope 210 is the same as the type of the previously connected endoscope 210. Vice versa, if the disconnection time is equal to or longer than the predetermined time, the connection scope determining circuit 140 determines that the type of the currently connected endoscope 210 is different from the type of the previously connected endoscope 210. This determination is, for example, the process in step S104 of the processes described with reference to FIG. 2. The other operations are the same as those in the first embodiment. It is also possible to adopt a configuration that is similar to that of the modification of the first embodiment.

As described above, when the endoscopic system 1 is being used, the cable connecting the image processing device 100 to the endoscope 210 may be twisted, and in order to untwist the cable, the endoscope 210 may be disconnected from the image processing device 100. It takes, for example, about ten seconds or more to untwist the cable. Thus, the threshold value for the determination of the disconnection time that is performed by the connection scope determining circuit 140 may be set to an appropriate time of about ten seconds or more. As a result of this, the connection scope determining circuit 140 can determine whether a removal of the endoscope 210 from the image processing device 100 is a temporary operation for untwisting the cable, that is, whether the type of the endoscope 210 is unchanged, or whether it is something else.

The endoscopic system 1 according to the second embodiment can obtain the same effects as the endoscopic system according to the first embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device comprising:
   an image processing circuit configured to process image data obtained from an endoscope, the image processing circuit being configurable according to an application of the endoscope; and
   at least one control circuit configured to:
      detect a connection state of the endoscope,
      measure, based on a detection result of the connection state, a disconnection time from when the endoscope is disconnected until the endoscope is reconnected,
      determine, when the disconnection time is shorter than a predetermined time, that a currently connected endoscope and a previously connected endoscope are configured for a same application type,
      reconfigure the image processing circuit according to the type of the currently connected endoscope when it is determined that the currently connected endoscope and the previously connected endoscope are not configured for the same application type, and
      not reconfigure the image processing circuit when it is determined that the currently connected endoscope and the previously connected endoscope are configured for the same application type.

2. The image processing device according to claim 1, further comprising a storage circuit configured to store the type of the previously connected endoscope.

3. The image processing device according to claim 2, wherein the at least one control circuit is configured to obtain, when it is determined that the currently connected endoscope and the previously connected endoscope are not configured for the same application type, information on the application type of the endoscope stored in the storage circuit.

4. The image processing device according to claim 1, wherein the image processing circuit is configured to change a circuit configuration of the image processing circuit to reconfigure the image processing circuit.

5. The image processing device according to claim 1, wherein the image processing circuit is configured to rewrite software of the image processing circuit to reconfigure the image processing circuit.

6. The image processing device according to claim 1, further comprising an image output circuit having a function to output the image data output from the image processing circuit to the outside of the image processing device, the image output circuit being configured to stop output of the image data to the outside of the image processing device when it is detected that the control circuit and the endoscope are disconnected.

7. The image processing device according to claim 1, wherein the currently connected endoscope is the same as the previously connected endoscope.

* * * * *